(12) United States Patent
Charette et al.

(10) Patent No.: US 10,006,874 B2
(45) Date of Patent: Jun. 26, 2018

(54) ALTERNATIVE FUELS ANALYZER

(71) Applicant: XRSciences LLC, Carlsbad, CA (US)

(72) Inventors: Colin Charette, Carlsbad, CA (US);
Thomas Atwell, Carlsbad, CA (US);
Tom Gibbons, Carlsbad, CA (US);
Jacob Lopp, Carlsbad, CA (US);
Chaur-Ming Shyu, Carlsbad, CA (US);
John Dascomb, Carlsbad, CA (US)

(73) Assignee: XRSciences, LLC, Carlsbad, CA (US)

( * ) Notice: Subject to any disclaimer, the term of this patent is extended or adjusted under 35 U.S.C. 154(b) by 0 days. days.

(21) Appl. No.: 14/888,929

(22) PCT Filed: May 2, 2014

(86) PCT No.: PCT/US2014/036681
§ 371 (c)(1),
(2) Date: Nov. 3, 2015

(87) PCT Pub. No.: WO2014/179757
PCT Pub. Date: Nov. 6, 2014

(65) Prior Publication Data
US 2016/0084776 A1    Mar. 24, 2016

Related U.S. Application Data

(60) Provisional application No. 61/854,894, filed on May 3, 2013.

(51) Int. Cl.
*G01N 23/222*    (2006.01)
*G01N 23/12*     (2018.01)
*G01T 3/00*      (2006.01)
*B07C 5/34*      (2006.01)
*C10L 5/48*      (2006.01)

(52) U.S. Cl.
CPC ............ *G01N 23/222* (2013.01); *B07C 5/34* (2013.01); *C10L 5/48* (2013.01); *G01N 23/12* (2013.01); *G01T 3/00* (2013.01); *C10L 2290/24* (2013.01); *C10L 2290/60* (2013.01)

(58) Field of Classification Search
CPC ............ G01N 23/222; B07C 5/34; C10L 5/48
See application file for complete search history.

(56) References Cited

U.S. PATENT DOCUMENTS 4,171,485 A * 10/1979 Marshall .............. G01N 23/222
                                                  250/255
5,383,612 A *  1/1995 Williams .................. F23K 1/00
                                                   241/34

(Continued)

FOREIGN PATENT DOCUMENTS

EP        1106674 A1    6/2001

OTHER PUBLICATIONS

International Search Report dated Dec. 10, 2014, issued for International Application No. PCT/JP2014/036681.

*Primary Examiner* — Hugh H Maupin
(74) *Attorney, Agent, or Firm* — Manuel de la Cerra

(57) ABSTRACT

A process for preparing alternative fuels so that it is acceptable for use in cement plants and other manufacturing processes is detailed. This includes a material analyzer that can detect trace contaminants in alternative fuels. This new analyzer, combined with an associated method of processing the alternative fuels allows users to blend the fuel to ensure that it is acceptable for plant operations.

14 Claims, 15 Drawing Sheets

(56) References Cited

U.S. PATENT DOCUMENTS

| | | | |
|---|---|---|---|
| 5,825,030 A * | 10/1998 | Hurwitz | G01N 23/04 |
| | | | 250/358.1 |
| RE36,943 E * | 11/2000 | Atwell | G01N 23/222 |
| | | | 198/811 |
| 2004/0141585 A1 | 7/2004 | Proctor | |
| 2007/0295911 A1 * | 12/2007 | Sved | G01T 3/00 |
| | | | 250/359.1 |
| 2009/0101827 A1 | 4/2009 | Harris et al. | |
| 2009/0133507 A1 | 5/2009 | Wolfschaffner | |
| 2010/0163734 A1 | 7/2010 | Proctor et al. | |
| 2012/0085686 A1 | 4/2012 | Radema et al. | |

* cited by examiner

ALTERNATIVE FUELS ANALYZER

FEDERALLY-SPONSORED RESEARCH OR DEVELOPMENT

This invention was made with Government support under grant no. 1248933 awarded by the National Science Foundation. The Government has certain rights to this invention.

TECHNICAL FIELD

The present invention relates generally to in-line analyzers, and is directed to an in-line analyzer for alternative fuels.

BACKGROUND

In line Prompt Gamma Neutron Activation Analysis (PG-NAA) analyzers are in wide use throughout the coal, cement, and minerals industries. These systems are used for measuring bulk material, such as rock material coming out of a mine. They do not just do a surface measurement such as X-ray fluorescence and X-ray diffraction, but the analysis is deeply penetrating, and can thus analyze large quantities of materials. The most prevalent type of PGNAA analyzer is an on-belt conveyor analyzer, where all of the material on the conveyor belt is analyzed.

A commercially successful PGNAA analyzer was a chute-type of analyzer, as shown in FIG. 1 and described in 1986 U.S. Pat. No. 4,582,992 to Atwell et al. titled "Self Contained, On-line, Real-Time Bulk Material Analyzer." Coal or rock produce was sent down the chute, and the material passing through the system was analyzed by the system. U.S. Pat. No. 4,582,992 describes that the PGNAA system was self-contained. These chute systems were very expensive and installation was very costly and difficult. This problem was solved with the development of on-line conveyor-belt PGNAA analyzers. One cross-belt analyzer is shown in FIGS. 2A and 2B, and described in 1995 U.S. Pat. No. 5,396,071 to Atwell et al. titled "Modularized Assembly for Bulk Material Analyzer". These cross-belt systems were significantly easier to install, and fit very well into the factory operations.

Since the first cross belt was developed, there have been a number of innovations to these cross-belt systems. The innovations have mainly focused on making the system easier to install and manufacture. For example, in U.S. Pat. No. 5,396,071 the belt analyzer was built in multiple identical segments. Segments on the bottom were made from the same mould, and segments on the top were made from a different mould. The central mould was modified to hold the source and detector. Thus this innovation focused on making it easier to build and assemble the analyzer. In Dec. 5, 2000 U.S. Pat. No. 6,157,034 to Griebel et al. titled "Flexible multiple-purpose modular assembly for a family of PGNAA bulk material analyzers," side modules are used on the conveyor belt analyzer such that the analyzer can be easily configured for different sizes of conveyor belts. This innovation again made it easier for installation and adjustment for different belt sizes, and it simplified manufacturing. In 2002, U.S. Pat. No. 6,657,189 to Atwell et al. titled "Maintaining Measurement Accuracy with Prompt Gamma Neutron Activation Analysis with Variable Material Flow Rates or Material Bed Depths," the system was designed to algorithmically correct for errors as a result of bed depth and flow rates. This patent was focused on reducing the error that varying flow rates and belt loading can cause in the PGNAA measurement. In W.O. Patent Application No. 2003056317 to Edwards et al. titled "Bulk Material Analyzer and Method of Assembly" discloses a system consisting of detectors and source into a C shape such that the system can slide from the side onto the conveyor belt, and then the other side is added. The main purpose of this design was for ease of installation, and also for simpler manufacturing of the analyzer.

In W.O. Patent Application No. 2008/021228 A3 to Atwell et al. titled "Bulk Material Assembly Including Structural Beams Containing Radiation shielding Material" focuses on making the system easier and less expensive to build, assemble and install. This patent application describes using structural beams that are filled with shielding material to make it faster and easier to install the analyzer, and also reduce the system cost. Thus the design benefit was for easier installation and reduced costs.

Aug. 31, 2010 U.S. Pat. No. 7,786,439 to Harris et al. titled "Detector Apparatus," discloses the idea of putting the multi-channel analyzer and the detector in a housing that includes a temperature controlled assembly. U.S. Pat. No. 7,778,783 to Lingren et al. titled "Method and apparatus for analysis of elements in bulk substance" discloses a method of stabilizing the spectra coming from the PGNAA analyzer.

Since the development of the first PGNAA on-belt analyzers, the designs have evolved, mainly with the focus of ease of installation and ease of manufacture. Modern PGNAA devices typically mount to the rails of a conveyor belt, do not require cutting of the conveyor belt, and can be installed and calibrated in a few days.

The performance of PGNAA analyzers has not improved dramatically over the 25 years since the systems were first commercialized, as the systems deliver adequate performance for process control for most applications.

The industry with the widest adoption of PGNAA is the cement industry, where the equipment is used to monitor and control the raw material used to make cement.

In the cement industry, there is growing demand for reducing energy costs by increasing the use of alternative fuels. Alternative fuels are materials that can be burned in the cement kiln to provide heat content, and is a replacement for coal and oil. Alternative fuels are byproducts from industrial or commercial operations and include paint, metal cleaning fluids, electronic industry solvents, tires, fly ash, rice hulls, plastics and other industrial or municipal waste. Typically cement plants can obtain these items at little or no cost, or in some cases are paid to burn.

For a cement plant to burn Alternative Fuels (AF), the AF generally includes three characteristics. The first characteristic is that the AF includes little to no elements that negatively impact the cement manufacturing process. For example, alternative fuels with too high a level of chlorine are generally unacceptable for cement plant operations. The Chlorine can turn into hydrochloric acid, and cause erosion in the kiln. Thus each AF end user has an upper limit specification on the amount of Chlorine. The second characteristic is that the AF must have a meaningful heat value, such that it is useful as a fuel. The third characteristic is that the material of the AF complies with environmental regulations. The U.S. regulations essentially state that to be acceptable, the AF cannot have contaminant levels greater than coal. This means that for AF to be acceptable for cement plants, elements such as mercury, arsenic, cadmium, lead, and other hazardous elements must be at a level that is at or below the level of coal.

Currently it is very expensive and time consuming in order to test and qualify new types of alternative fuels. There are companies that specialize in blending alternative fuel for cement plants. The vast majority of these get a very specific and consistent type of feedstock, and they do not work with multiple different materials. Only a very few companies blend varying stock of AF because of the difficulties and challenges in ensuring that the material is suitable for plant operations.

Another factor that makes this issue particularly challenging is that testing AF for trace elements requires very low detection levels that may not possible with conventional PGNAA systems. Thus for receiving a wide variety of alternative fuels, an expensive lab may be required to analyze the AF. A lab can test only a very small sample, and thus may not be a valid way of characterizing the AF.

SUMMARY OF THE DISCLOSURE

The PGNAA analyzer disclosed herein may deliver a significantly higher performance than conventional PGNAA analyzers and is designed to deliver performance suitable for analyzing alternative fuels for major mineral content that ultimately blends with the quarry rock and sand mineral content cement plants use such as Si, Al, Fe, Ca, Mg, S, K, Na, Mn, Ti, P—most as oxides) and detecting and measuring trace contaminants. Further, in embodiments disclosed herein, the PGNAA measurement information may be used to prepare a blend of AF with an elemental composition that is acceptable for plant operations. Additionally, the measurement data provided by the analyzer may be used to prepare the AF to specific target heat content (such as BTU/lb).

Conventional PGNAA systems may not be capable of measuring to the detection level required to accurately measure trace elements in a material. The PGNAA analyzer disclosed herein includes a geometry that may increase the signal and performance of PGNAA systems, such as the system shown in FIG. 6. In embodiments, the PGNAA analyzer includes a flat bottom belt with vertical sidewalls that may deliver a higher efficiency than a conventional PGNAA analyzer because it may provide an optimum geometry to locate arrays of detectors on all sides of the material. The PGNAA analyzer geometry may include a portion of the source side when adequate neutron shielding placed between the source and the detectors on each side of the source. This geometry may not be a good fit for the type of conveyor belts common to the cement, coal and minerals industries, because these are 'trough-shaped belts with 20 to 45 degree angles.

In embodiments, the PGNAA analyzer disclosed herein includes modern high speed electronics, which combined with this new geometry can improve the measurement performance of PGNAA by a factor of 5 to 10× or more. The exact performance improvement depends on other factors such as the density of the material, the elemental composition of the material (e.g., the percentage of hydrogen generally boosts the signal from all other elements due to hydrogen's strong moderation effect on the source neutrons), and so forth.

The PGNAA analyzer including modern high speed electronics may be able to measure down to trace levels for such things as Mercury, Arsenic, Cadmium, and other trace elements.

The system with this or a similar geometry can also be used to analyze raw material, coal, minerals, and other bulk material with significantly higher performance than conventional PGNAA systems. So this invention is not limited to AF but to waste and any material put in or through the system.

In embodiments, this new high performance analyzer can be used in a blending process to blend AF so that it meets target composition. These embodiments include a method of blending the AF to meet target specifications such as target composition and heat content (BTU/lb) so that it can be suitable replacement for coal, oil, and other fuels. This design is made to prepare the AF for the cement market, but the fuel can be used in any market that can benefit from replacing coal, oil, and other fuels and for blending material to meet specific material properties.

DETAILED DESCRIPTION OF THE DRAWINGS

Figure 1:
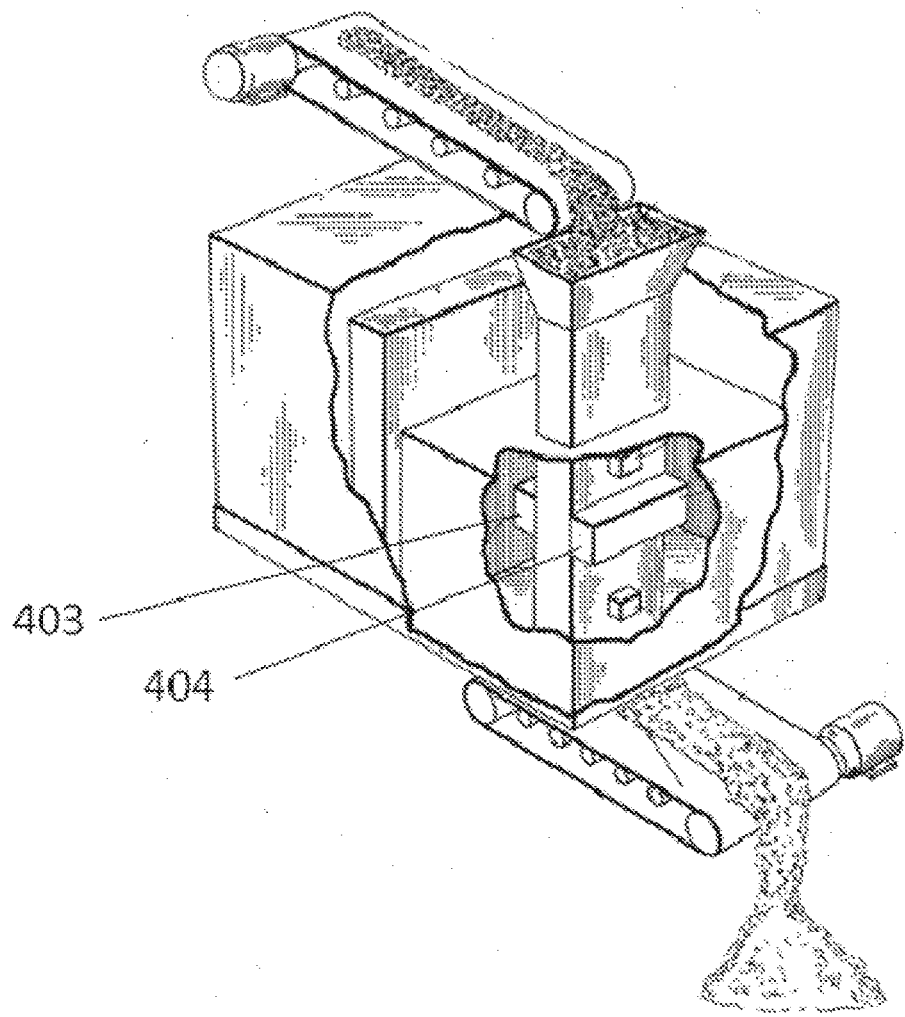
FIG. 1 is a perspective view of a chute analyzer.
Figure 2A:
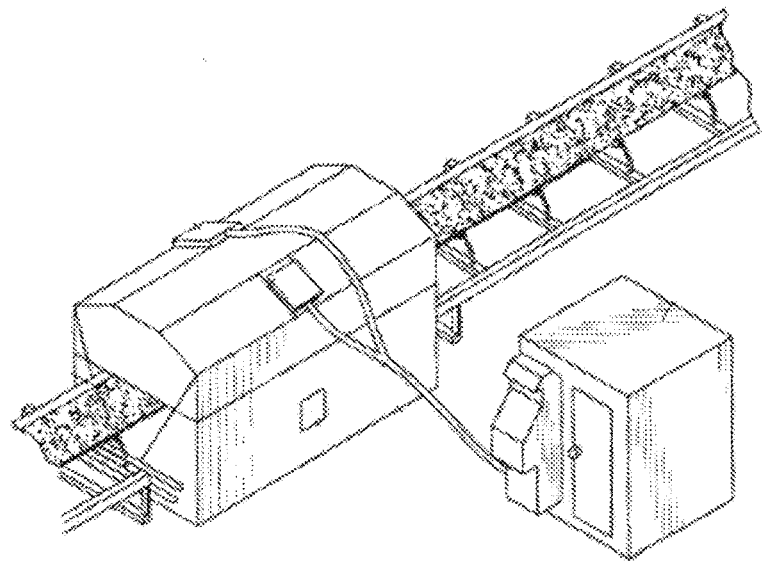
FIG. 2A is a perspective view of a conveyor belt analyzer.
Figure 2B:
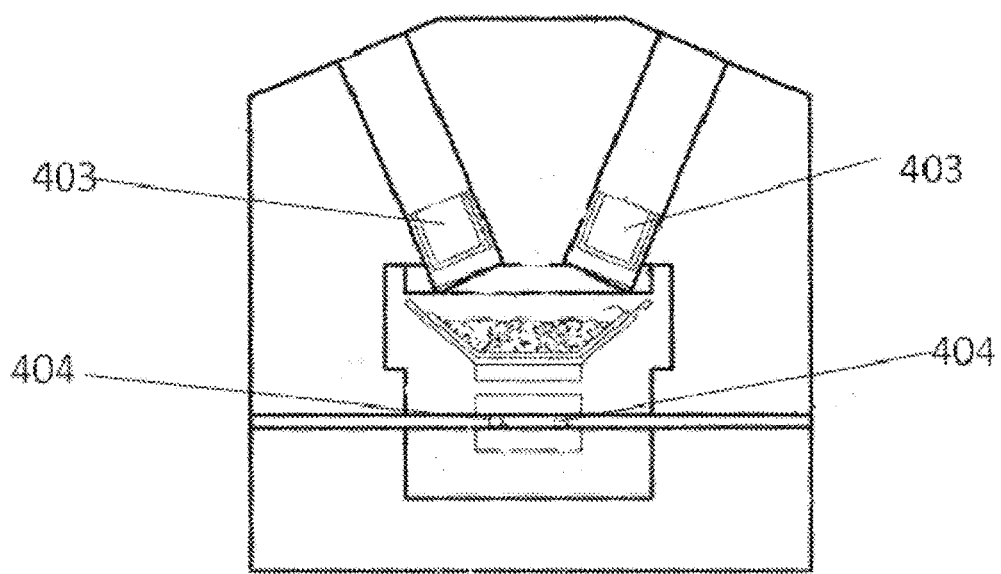
FIG. 2B is a side view of a conveyor belt analyzer.
Figure 3:
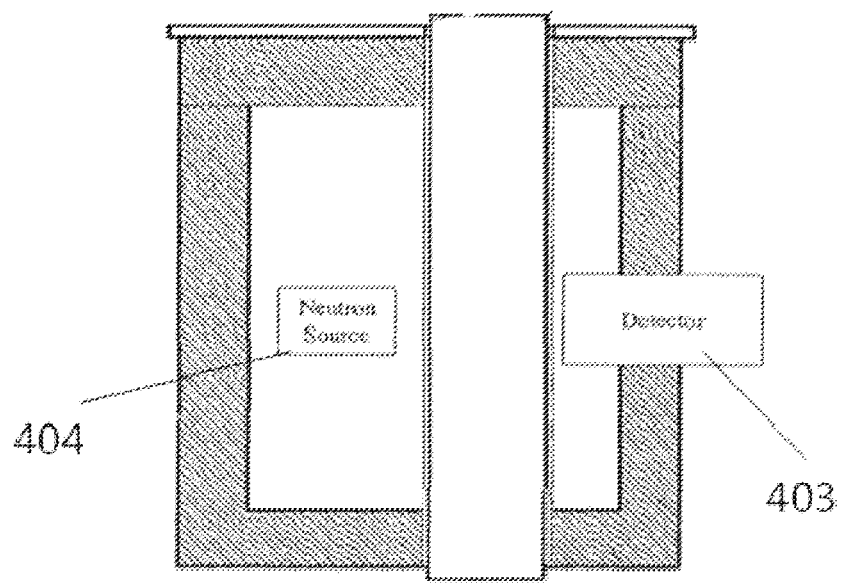
FIG. 3 is a diagram of an analyzer where the material flows thorough the analyzer. This configuration may be used for a static analyzer, or a slurry analyzer.

There have been several different types of PGNAA analyzers that have been developed over the past 25 years. These include a chute analyzer shown in FIG. 1, a conveyor analyzer, shown in FIG. 2, and a pipe analyzer where the material is analyzed either when it is not moving or when it is passing through the system, as shown in FIG. 3. These systems take bulk material in solid or liquid form, and analyze the material. These systems and in particular the conveyor belt analyzer are used in the coal, cement, and minerals industries.

Figure 4:
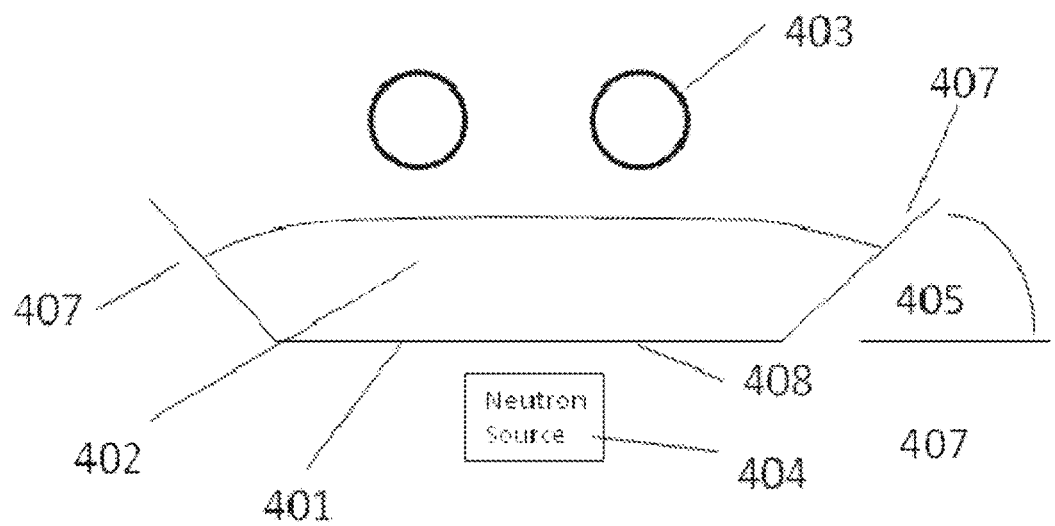
FIG. 4 is a schematic illustration showing conventional conveyor belt analyzer.
Figure 5:
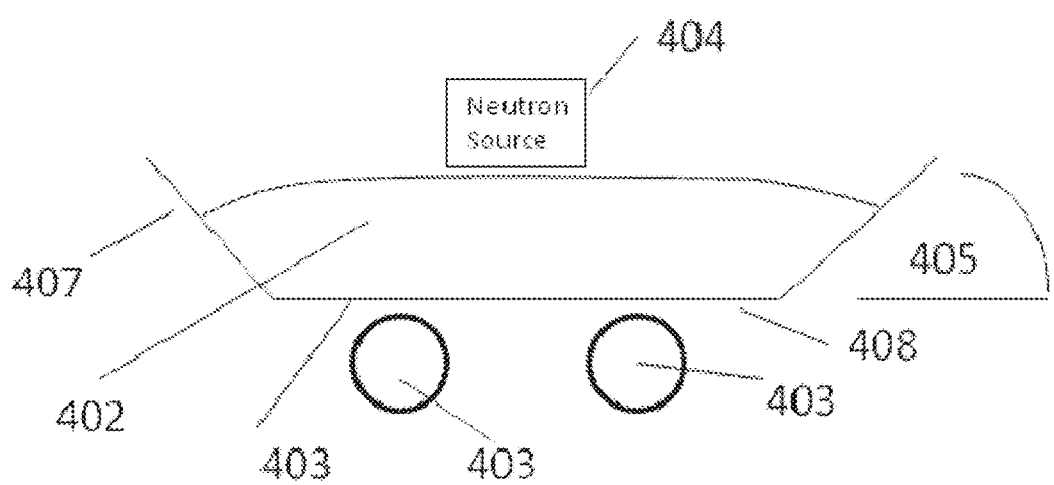
FIG. 5 is a schematic illustration showing another conventional conveyor belt analyzer.

By far the most predominant type of PGNAA analyzer is an on-belt conveyor analyzer, where the material is transported on a conveyor belt. A conveyor belt analyzer is shown in FIG. 4, where the neutron source 404 is on the bottom, the belt 401 holds the material 402, and the detectors 403 are located above the material 402. This is a typical geometry for a cement analyzer. Another configuration, shown in FIG. 5 is where the conveyor belt is the same, but the neutron source is on the top above the material, and the detectors are below the belt. This is a common configuration for coal PGNAA analyzers.

In a conveyor system, the conveyor belt is typically held in place using toughing belt idler assemblies. The vast majority of toughing belt idler assemblies that hold the conveyor belt result in an angle 405 that is at a maximum of 45 degrees.

Figure 6:
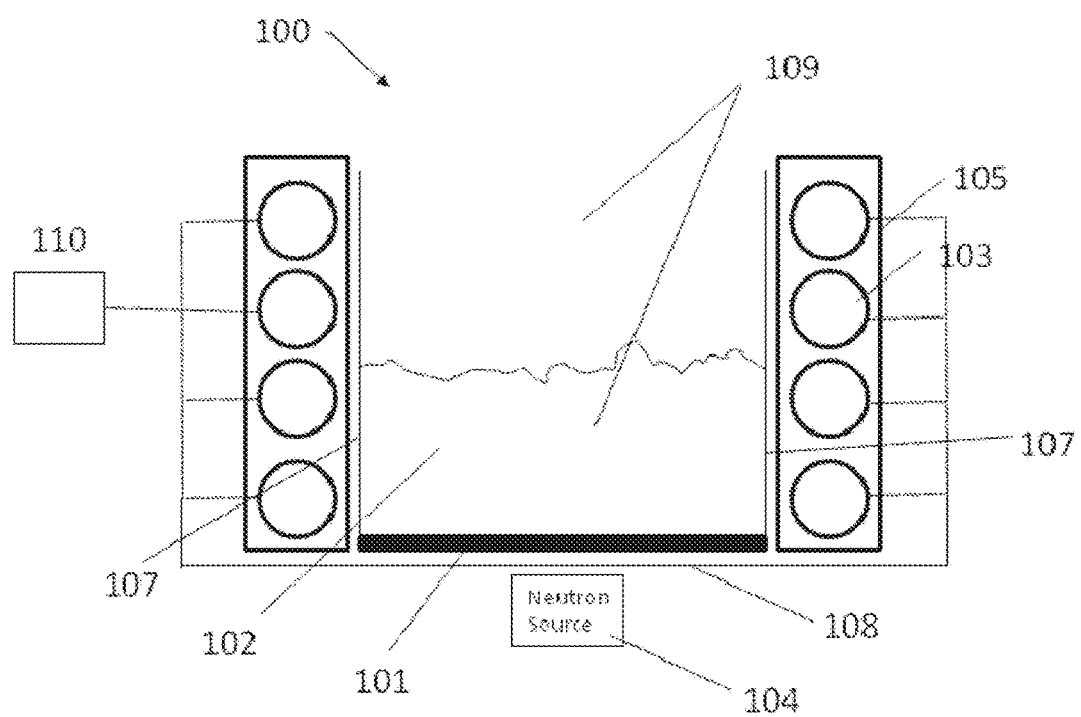
FIG. 6 is a schematic illustration of one embodiment of a high performance analyzer.

FIG. 6 is a schematic illustration of one embodiment of a high performance analyzer 100. In the embodiment illustrated, the PGNAA analyzer 100 includes a conveying mechanism 108. The conveying mechanism 108 includes a conveyor 101 with a flat bottom belt. The conveying mechanism 108 may also include sidewalls 107 adjacent conveyor 101 extending at least partially in the vertical direction. The Conveyor 101 and the sidewalls 107 may form a detection zone 109. This detection zone is the area that the material travels where the material is analyzed.

In some embodiments, the conveying mechanism may be rectangular shaped as show in FIG. 6 and may include substantially vertical sides 107. In other embodiments, the conveying mechanism 108 may be trough shaped with the sides 107 angled greater than 50 degrees from the horizontal and up to 130 degrees relative to the conveyor 101. In another embodiment, the sides 107 are angled from 40 degrees to 130 degrees relative to the conveyor 101. In another embodiment, the sides 107 are angled from 90 degrees to 120 degrees relative to the conveyor 101. In still a further embodiment, the sides 107 are angled from 90 degrees to 120 degrees relative to the conveyor 101.

The analyzer 100, as shown in the preferred embodiment in FIG. 6, and alternate embodiments in FIG. 7, FIGS. 8A, 8B, and 8C include locating at least one neutron source 104 proximate the detection zone 109. In the embodiment illustrated in FIG. 6, the neutron source 104 is proximate the conveyor 101 and below the conveyor 101. In the embodiment illustrated in FIG. 7, the neutron source is located above the detection zone 107, opposite the conveyor 101. In the embodiment in FIG. 8C, the neutron source is located on the side of the conveyor, proximate the detection zone 109, and the conveyor 101 acts as part of the sidewall of the analyzer 100.

As illustrated in FIG. 6, the detectors 103 are positioned proximate the detection zone 109 along a side of the detection zone 109 adjacent the location of the neutron source 104.

Figure 7:
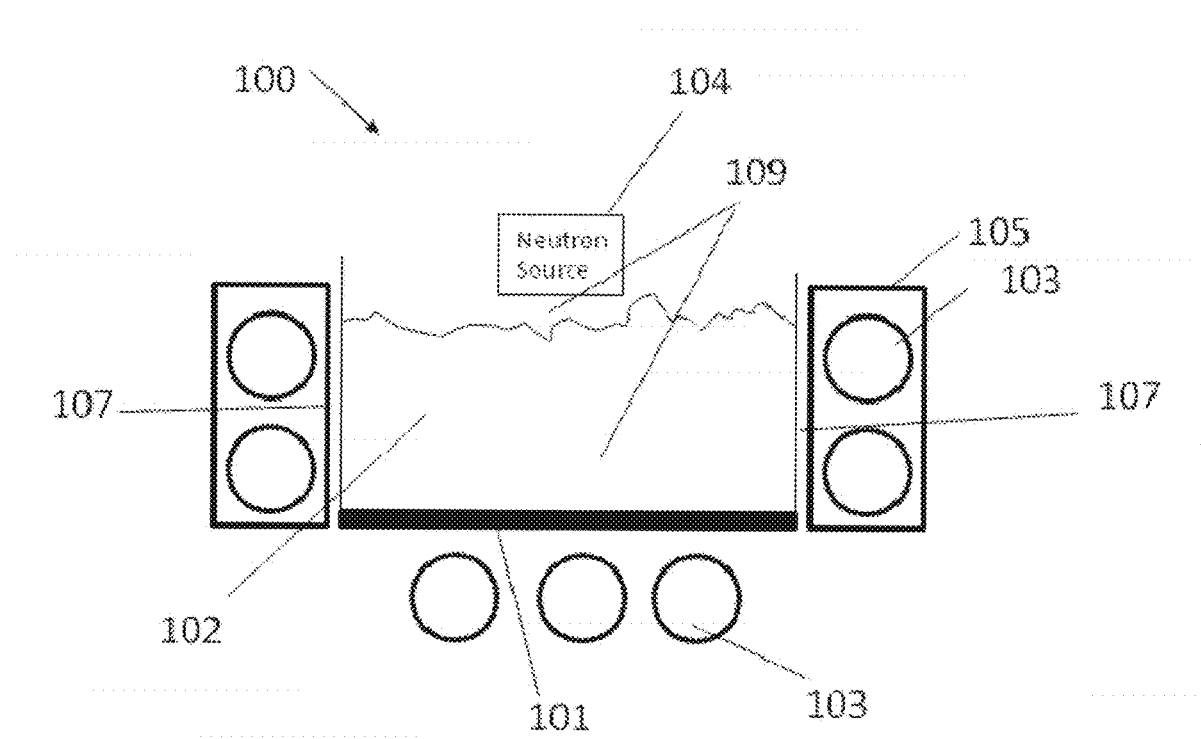
FIG. 7 is a schematic illustration of an alternate embodiment of the high performance analyzer of FIG. 6.
Figure 8A:
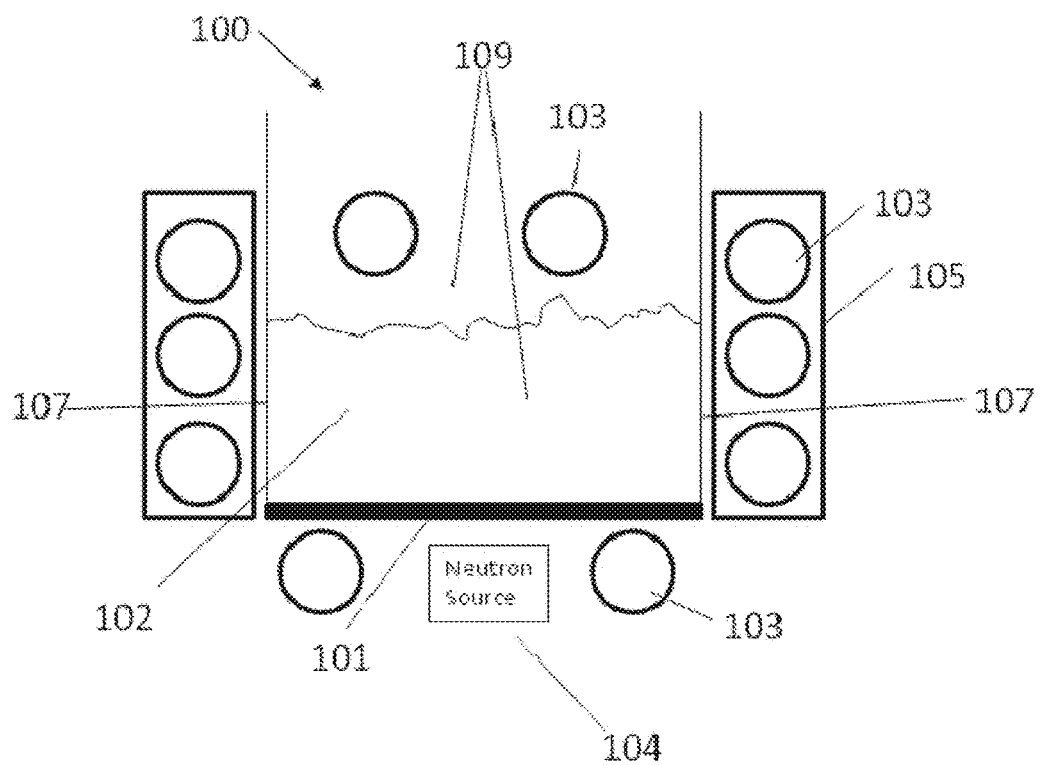
FIG. 8A is a schematic illustration of an alternate embodiment of the high performance analyzer of FIGS. 6 and 7.
Figure 8B:
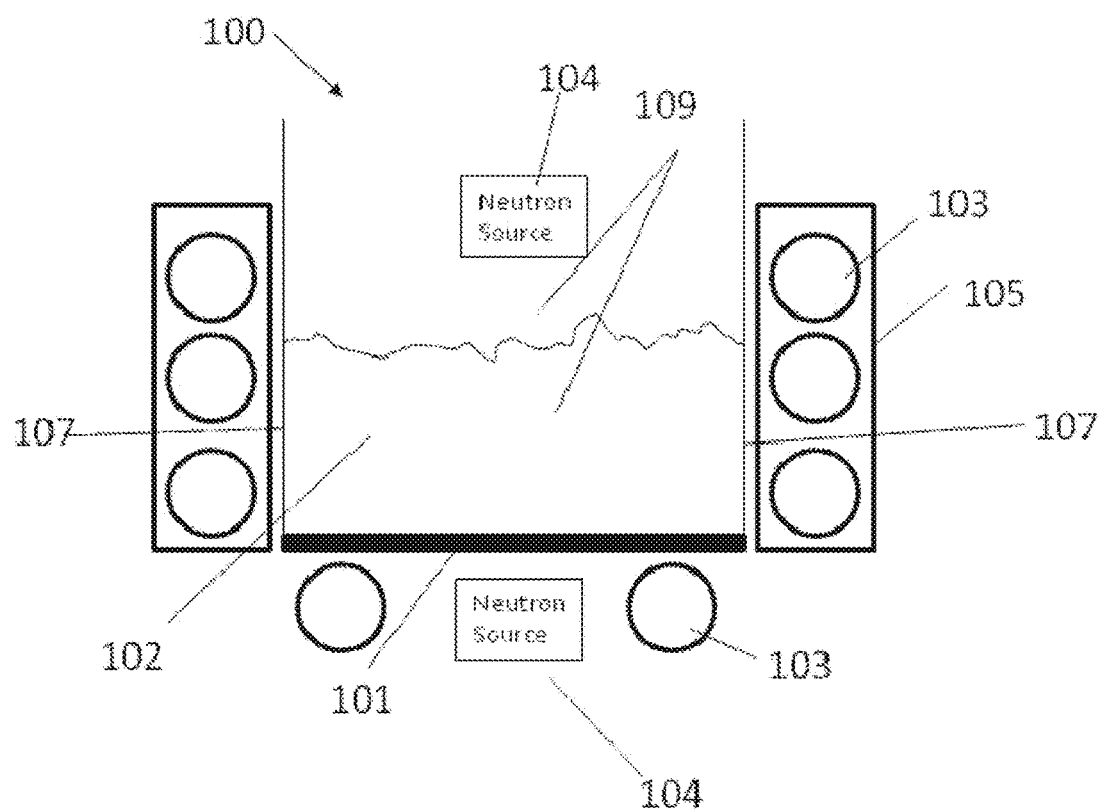
FIG. 8B is a schematic illustration of an alternate embodiment of the high performance analyzer of FIGS. 6 and 7.
Figure 8C:
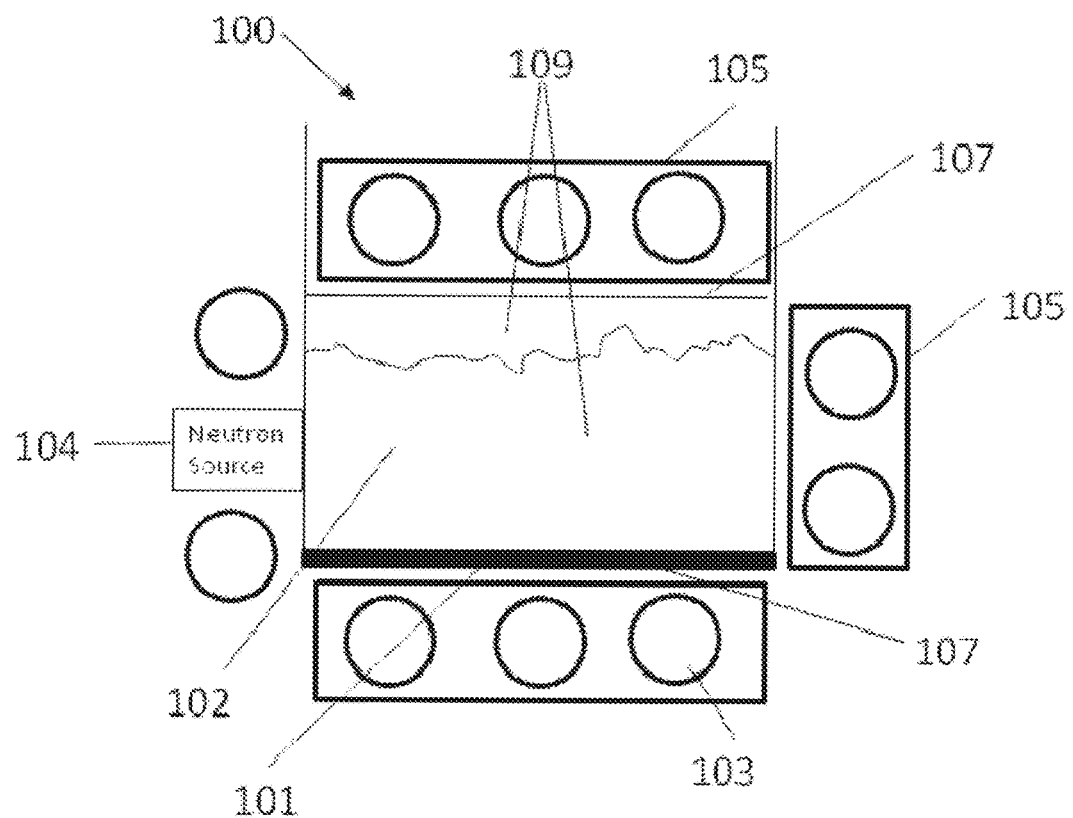
FIG. 8C is a schematic illustration of an alternate embodiment of the high performance analyzer.

Detectors 103 may be positioned on one side, or both sides of the side walls 107. As illustrated in FIGS. 7, 8A, and 8C, detectors 103 can additionally be positioned opposite the neutron source 104 for additional signal. As illustrated in FIG. 7, the neutron source 104 may be above the material being analyzed. An alternate embodiment as illustrated in FIG. 8C is to place the source to the side of the material being analyzed. One or multiple detectors 103 can be used to increase the overall signal from the analyzer 100. The detectors 103 can be horizontal to the belt as shown in FIG. 6, or vertical, or any orientation on the sides, which may increase the geometric efficiency of the PGNAA system. Arrays 105 of detectors 103 may also be used in the various locations for detectors described herein. In some embodiments, the analyzer 100 may also include an array of neutron sources 104.

The analyzer 100 may also include a controller 110. The controller 110 may be configured to receive the signals from the detectors 103 and may be configured to process the signals received to determine the composition of bulk material, such as an alternative fuel source and to determine the amount of trace elements, such as contaminants that are within the composition. The controller 110 may also be configured to sort the bulk material based on its composition by directing the bulk material to two or more locations based on the composition of the bulk material, such as by directing a diverter gate into various positions to divert the bulk material into different directions. The controller 110 may also be configured to determine the calorific value of the bulk material, such as alternative fuel sources based on the measured composition of the bulk material.

The configurations disclosed herein may situate the detectors 103 closer to the material that emits the gamma rays after the neutron source 104 emits the neutrons into the material, which may improve the signal. In embodiments, the source may be partially in the material. The exact location that is optimum may depend on the material, and the constraints of the system.

In our preferred embodiment, the belt is flat or close to being flat with substantially vertical sides. In an alternate embodiment, the conveyor belt system includes sides that are gradually rolled vertically to form a tube. A circular array of detectors can be placed around the belt. The sides, such as the vertical or gradually rolled sides, can be made of different materials, but in the preferred embodiment they are made of a material that can absorb and reflect the neutrons, such as polyethylene.

Note that the sides do not have to be perfectly vertical, and the bottom belt does not have to be perfectly horizontal. Unlike other on-belt analyzers that have the detectors on the top or the bottom, with this design the detectors are on the side of the material under analysis. The detectors located on the substantially vertical sides of the belt may place the detectors and source closer to the analysis region, while still allowing for use of a conveyor mechanism.

There are other aspects to the design that are common to PGNAA systems. For example, the detectors are generally shielded from neutrons entering the detector. A combination of polyethylene, boron, and other materials may be used to shield the detectors from the neutrons. The system may include biological shielding for radiation safety. The neutron source, if an isotope, typically has bismuth to block gamma rays emitted from the isotopic source. When a D-T generator is used, additional shielding material may be required for biological shielding, as well as to shield the detectors.

Figure 13:
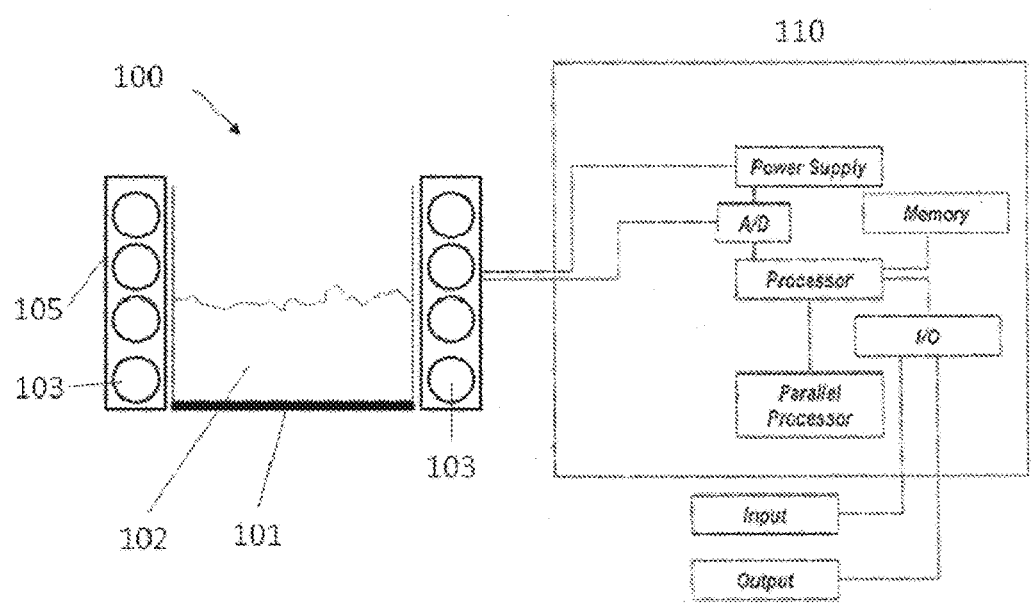
FIG. 13 is a functional block diagram of an analyzing system.

A typical analysis approach is shown in FIG. 13. In the preferred embodiment, the gamma ray spectra from each gamma detector is captured by a Analog-to-digital board, and this data is analyzed by a processing module of the controller 110. In the embodiment illustrated in FIG. 13, the controller 110 is a computer. However there are many combinations of detector gamma ray processing configurations that are acceptable. The resulting analysis can be displayed on a monitor, or provided over the web. The computer would typically communicate with some other equipment as part of this process. For example, a belt scale may be used to send the weight information to the analyzer, and this would be used in the analysis. Similarly, a moisture meter, or other sensor can be configured and used with the information. In the case of blending or screening of material, the computer may interface to blending software to control and guide the blending process. There are a number of external sensors that may be configured with the system, and there may be a number of different devices and systems that may take the data and information from the system. Typically the resulting spectral data coming from the detector is analyzed using library least squares analysis, or multivariate analysis. However, there are other approaches that are possible such as comparison of spectra, peak analysis of spectra, chemometrics, or other ways to extract the elemental information from the gamma spectra.

Figure 14:
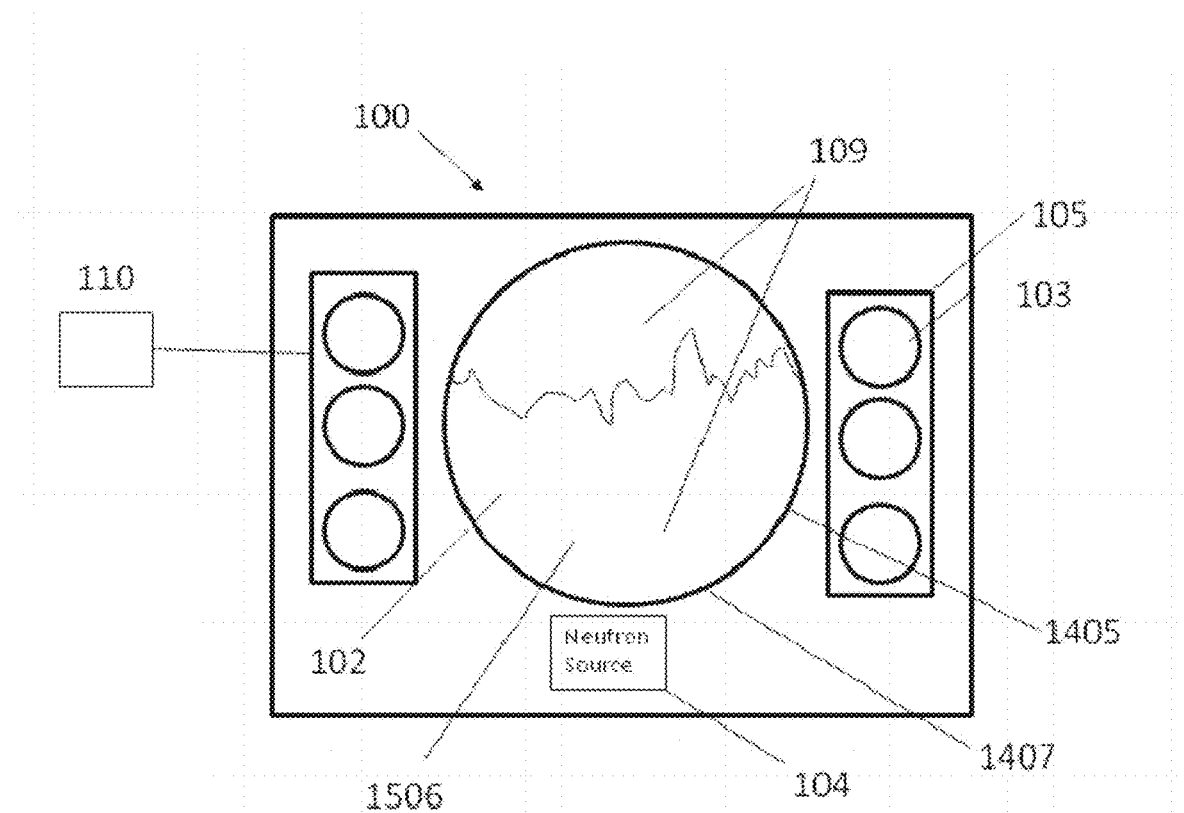
FIG. 14 is a functional block diagram of an analyzing system where the material is transported in a pipe.
Figure 15:
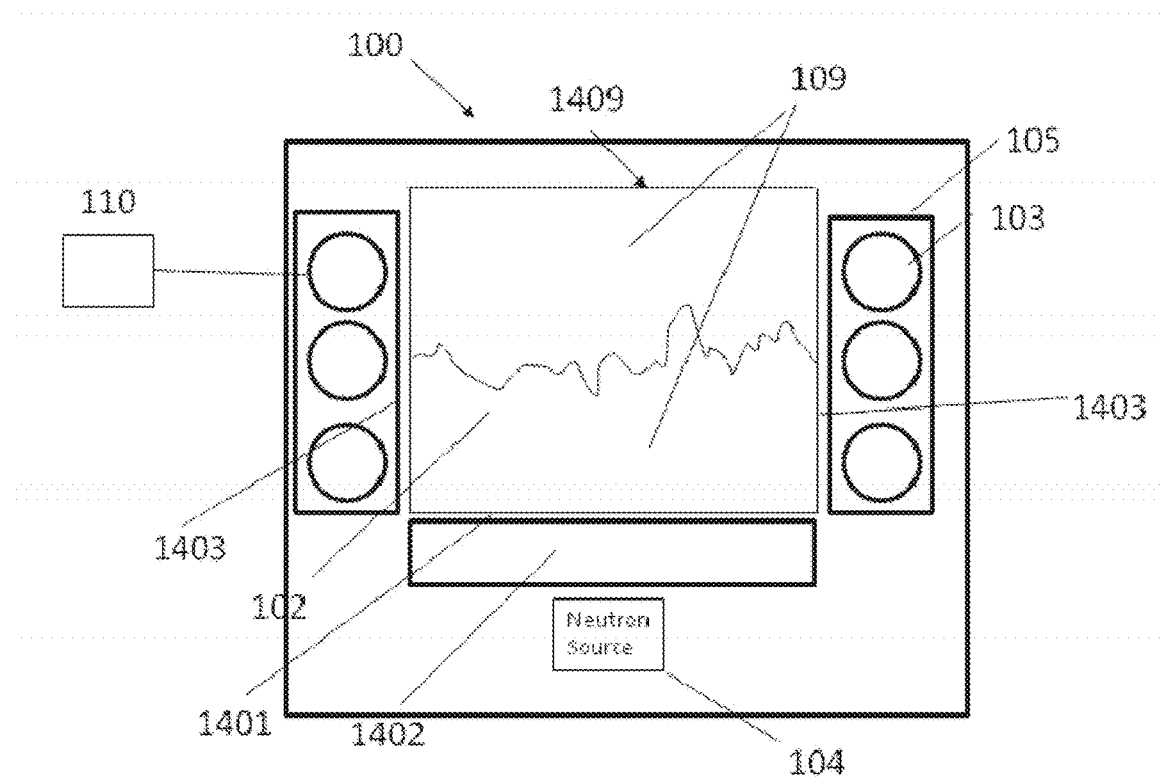
FIG. 15 is a functional block diagram of an analyzing system where the material is transported in a air-slide.

In this document, we refer to PGNAA. However, in our preferred embodiment, we are using a neutron generator as a source of neutrons, and Pulsed Fast Thermal Neutron Analysis (PFTNA) so that that it is possible to extract additional measurement information such as the carbon, oxygen, and nitrogen measurement information. PGNAA does not provide these measurements, but PFTNA does provide these measurements. However, the technology can be Thermal Neutron Analysis (TNA), PFNA, and PFTNA, or other variations that are common in the industry. We refer to PGNAA, but it can be substituted for PFTNA, TNA, PFNA, or other neutron activation analysis methods. In a preferred embodiment, we are using a conveyor belt to transport the material. This is because conveyor belts are a very common method of transporting material. However, this can include other conveying means, such as a pipe, a pipe with a square cross section, apron-chain conveyor, an air slide, or other means of transporting the material. These transport methods can be configured with a similar geometry for higher performance. FIG. 14 shows the material being transported through a pipe 1407. The pipe would typically be of a low cross section material, such as a zirconium alloy. The detectors 1-3 are shown in an array, but they can be configured to be closer to the sides of the pipe 1407. As with other analyzer, there will be shielding between the neutron source and the detectors. The source can be pulsed or continuous neutron source. FIG. 15 shows an alternate embodiment where the conveyor includes an air-slide. In the embodiment illustrated, the conveyor includes an air chamber 1402 and a porous material 1401 that allows air to pass to the main transport chamber 1409. The main transport chamber 1409 includes sides 1403 adjacent the porous material 1401 and a top 1409. Top 1409 may extend from one side 1403 to the other side 1403. Top 1409 is located opposite porous material 1401 relative to the main transport chamber 1409 and the detection zone 109. The main transport chamber 1409 encloses around the detection zone 109. The air chamber 1402 is located next to the main transport chamber 1409 and is separated from the main transport chamber 1409 by the porous material 1401 The air from the air chamber travels through the porous material 1401, and fluidizes the material being transported 102. The air slide is angled on a slight angle from horizontal to convey the material down the air slide. The conveyor/air slide section in the analyzer may also be made of material that has a low neutron cross section such as carbon fiber to minimize the signal from the air chamber structural material. Similarly the porous material may be composed of a material with a lower cross section material. The detectors are positioned to optimize the signal in the detection zone 109. In FIG. 14. and FIG. 15. additional shielding material and moderation material may be used between the neutron source and the material and detectors to optimize the signal from the material 102. As with the conveyor belt solution, the detectors may be located on the sides and adjacent to the neutrons source, or in the other configurations and embodiments possible to those skilled in the art. As there are other methods of conveying material than conveyor belts, we refer to conveyor as a means of transporting the material, whether a conveyor belt, pipe, air slide or other conveying means.

We are using PFTNA in our preferred embodiment, because this produces measurements that are not possible with PGNAA. For example, PFTNA can measure carbon, oxygen, and nitrogen. Using these and PGNAA measurements, combined with external measurements such as the moisture or belt loading, the measurements can be used to estimate the calorific value (one expression is BTU/lb) of the AF.

Many different algorithms and equations are possible to estimate the BTU/lb or similarly to estimate the moisture content of the material under analysis. The Carbon, Oxygen, and Nitrogen measurements and other measurements in this equation are provided by the analyzer, as well as with possible associated additional measurement equipment combined with this system. An example of how to estimate the calorific value of the material is to use a linear combination of elements. This can be in the form of BTU/lb equals A1*carbon_measurent+A2*oxygen_measurement+A3*hydrogen_measurement+AN*N_Measurement, where A1, A2, A3 coefficients, and AN*N_Measurement represents other coefficients and measurements that are used to calculate the calorific value. This is just one example of calculating the calorific value. Many different equations using the analyzer measurement values with possibly additional measurements from other equipment can be used to calculate the heat value. We refer to heat value and Btu/lb. This refers to the heat content, often expressed as BTU/lb of the fuel. However, our objective is to produce a heat value that can be compared to coal or other fuels, whether this is in lbs, kg, an integrated value, or other methods or units used to express the heating value of the material.

Various scenario and use models are possible with this configuration. It may be possible to just analyze the AF to ensure and verify that the AF has suitable properties acceptable for use in a cement plant. Another use model is to use the analyzer to blend the AF to provide a more consistent fuel.

Figure 9:
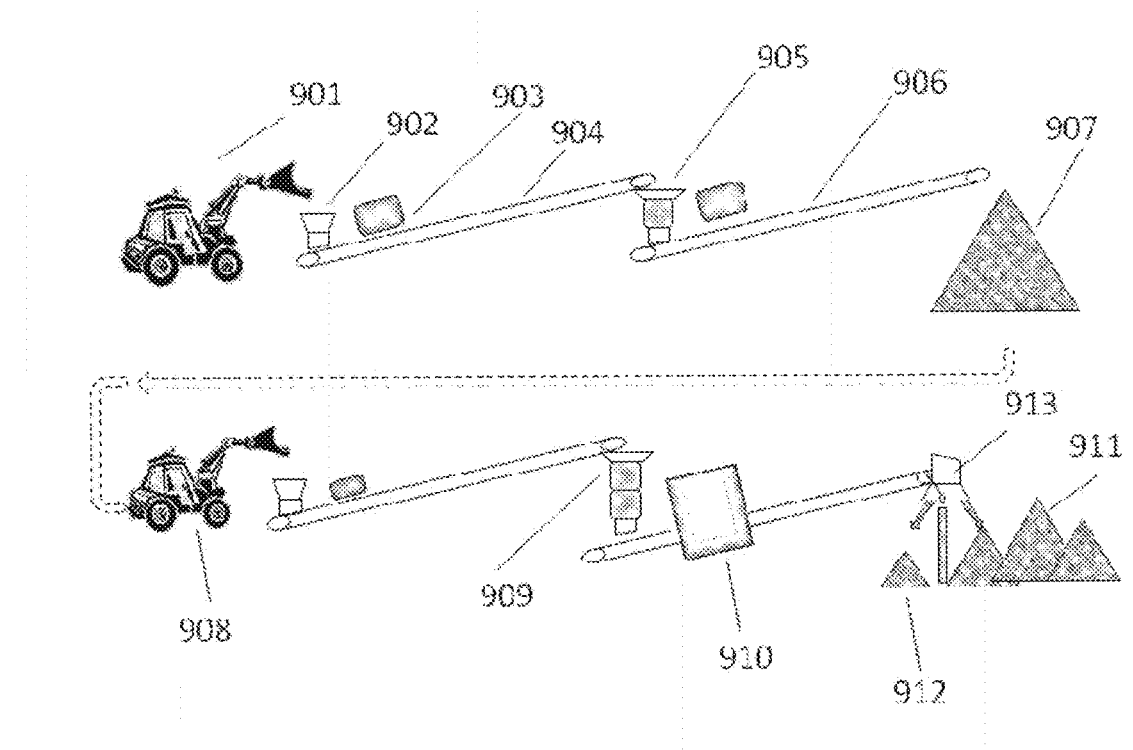
FIG. 9 is a schematic illustration of a system for shredding, analyzing and blending alternative fuels.

Sorting followed by Gravimetric Blending utilizing individual weigh-feeders on each sorted stockpile that meter out a precisely controllable mass flow rate that when combined achieves a target blend. This can be done in many different ways. An example of a blending system is shown in FIG. 9. A fork lift 901 takes the alternative fuels and puts the material into a hopper 902. The AF is then conveyed 904 to a shredder 905. The AF is shredded, and then conveyed 906 to a coarse shredded pile 907. Magnets to pull off steel can be used in this process 903, and at other locations. The AF is then transported, either on a conveyor or by fork lift to another hopper and conveyed to two-stage shredder 909. Thus the material comes out triple-shredded. The AF material is then run through the analyzer 910. This analyzer provides the elemental information of the triple-shredded Alternative Fuel. The material then is placed in one or more piles 911 912. The composition of each pile is known from the measurement from the sensor 910. Thus these piles can be gravimetrically blended to get a more consistent product or a pile of unacceptable material can be sorted using a diverter 913. The diverter 91 may be controlled by the controller 110. If there are any contaminants or unwanted contaminants, a pile may be unacceptable for use as AF 3. There are several ways to handle rejected material. The first is to blend small amounts of rejected material with this with other piles that may have none or a near-negligible amount of undesired trace minerals, such that the overall blend is acceptable. The second approach is to have the pile hauled to a landfill.

An enhancement of this blending operation is to correct and adjust the material in the piles so that it has the required characteristics. For example, it is possible that the closer the characteristics of the AF is to a customer's requirements, and the more consistent the fuel, the more valuable the fuel. If a specific BTU/lb is desirable, then blending can be done such that the AF has the required BTU/lb. To blend the fuel to a specific BTU content, AF with known high BTU material may be triple shredded and added to one pile. Alternatively, a low BTU/lb pile can be made with lower BTU/lb material. Using the average BTU/lb of each pile, a ratio of the two materials can be blended to give a specific BTU/lb value. A specific example can be used to clarify this. Assume one pile is 5000 BTU/lb, and the other pile is 10,000 BTU/lb, then a 50%/50% blend will result in a pile with a BTU of approximately 7,500 BTU/lb. Another approach is to blend while the material is being analyzed. For example, assume one pile has a 5,000 BTU/lb average, and then higher BTU material is run and added to the pile. The material with the higher BTU/lb is sent through the triple shredding process, and then the measured BTU information of this material is mass-integrated with the original pile to build up a pile to a target BTU level. Using this approach, a pile can be built that has the required BTU/lb value.

Yet another approach is to take the shredded alternative fuel, and placing this in a large layered pile. As a layer is placed on the pile, the composition of the AF material and location of the AF material is recorded. Layer after layer of AF are built up on horizontal layers. If the pile is layered horizontally, then the AF will be reclaimed/extracted vertically, and thus will represent an average for the material. Prior to the extraction, corrective material is added to the pile. For example, if a region in the pile has a low BTU/lb, then high BTU/lb material is added at that location. This may be AF, or alternately it may be another fuel such as coal that is added. The high BTU/lb material is added to the location with the lower BTU. In this way, the pile is built up such that it has a composition that is controlled and built to target specifications. Reclaiming of the pile is done vertically, effectively averaging or integrating the material such that the resulting blend is consistent and at target specifications.

Figure 10:
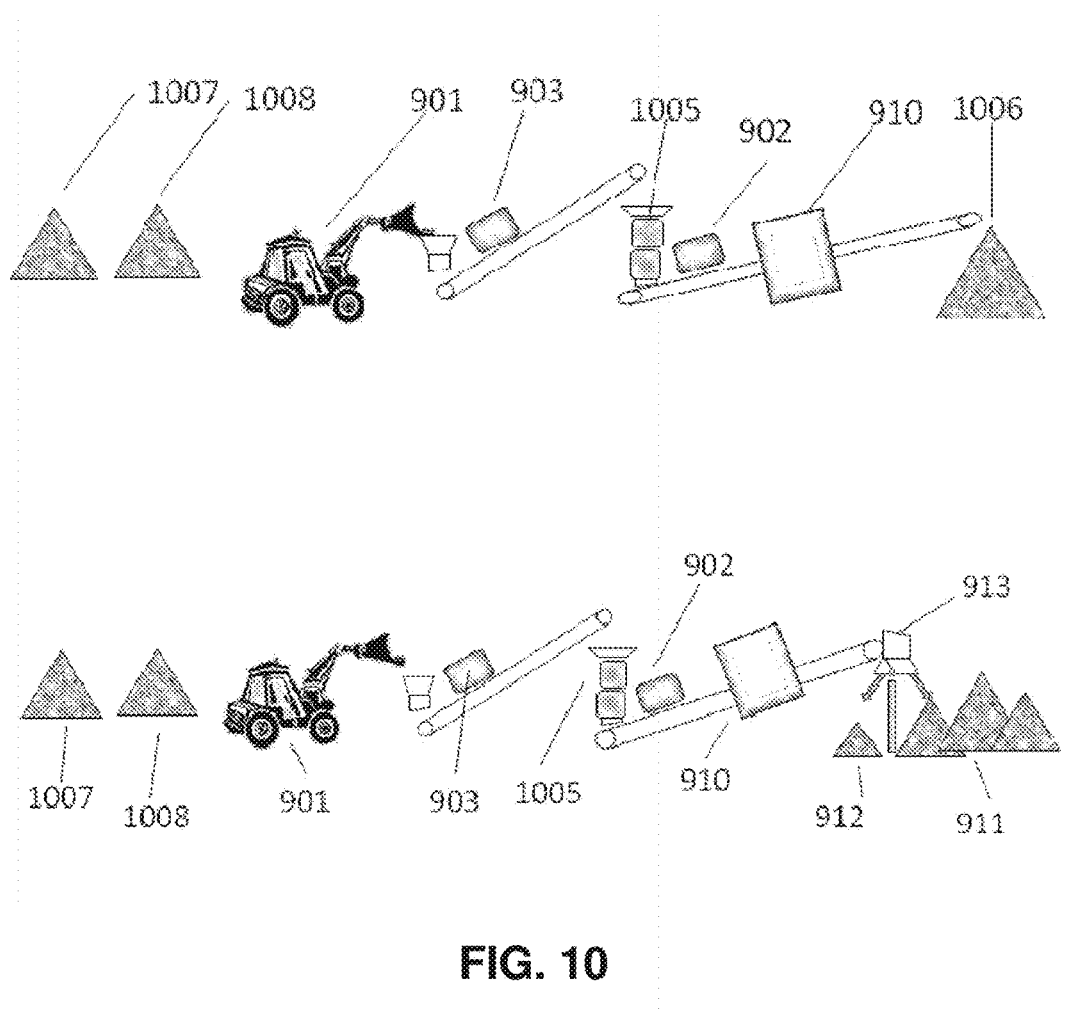
FIG. 10 provides additional configurations for preparing alternative fuels.

Two other blending approaches are illustrated in FIG. 10. In the top figure, there are two or more piles of AF. One pile 1007 has high BTU material, while another pile 1008 has lower BTU material. The material is placed on the conveyor belt or transport mechanism, either by fork lift in this case, or by other means such as silos. The material is then conveyed to be shredded. A triple shredding of the material can be done 1005 to ensure that the AF is well shredded, and in small pieces to aid in material transport and to help blending. There are cases where no shredding is required, but in this example the material is triple shredded, and then put through the analyzer 910. The material is then placed in a pile 1006. By using the analyzer measurements for feedback, and using this information to adjust the amount of material 1008 and 1007 that is used, this system can be designed to build a pile that meets specific target composition. The pile 1006 may be used, or may be further mixed or blended to further reduce the fuel variability.

In the blending example in the bottom of FIG. 10, the material is taken off the piles, shredded 1005 and run through the analyzer 910. Some form of diverter gate 913 can be used to build up different separate piles 911 912, or alternately any material that has unwanted contaminants can be sorted out 912. This process would be used in cases where there is the potential of material that is not acceptable and that needs to be separated from the rest of the AF.

The simplest way to use this system is to run the material through the analyzer, whether it requires shredding or not, and to place the material in a pile or container. The analysis can then be used to verify that the material is acceptable for plant operations, or the measurement information can be used to decide whether the material is not acceptable.

Figure 11:
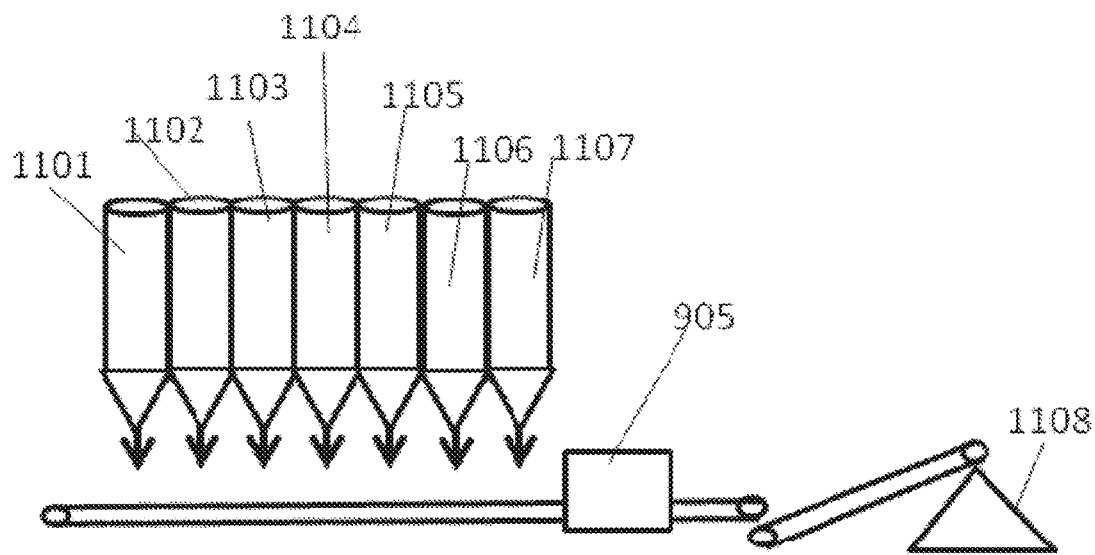
FIG. 11 is a schematic illustration of a blending system.

The blending of materials does not have to be limited to two materials, or just to waste or alternative fuels. Many different additives can be used. FIG. 11 shows a system where there are 7 additives that can be used to blend the material to a final composition. The material in the silos 1101 to 1107 can be any material, such as AF, waste, iron, silicon, plastic beads, or other materials that may be used to blend to pile 1108. The analyzer 905 is used to monitor the composition of the material and allows the operators to blend to a specific composition and/or heat content of the pile 1108. This pile in turn may not be the end product, but may be mixed or blended, or used with other material. This approach has the benefit of being able to blend the pile to a range of values that is desirable for the blend pile 1108. This does not have to be for the cement industry, it can be for any industry that can benefit from combing the material in a controlled fashion to product the pile 1008. For producing a fuel, the silos might include one silo with high BTU/lb AF, and another silo with lower BTU/lb material, and this is used to control the output blend. Alternately, low Btu/lb material may be added to the belt before or after the silos and the material in the silos used to adjust the mixture. Note that we are using silos in this example, but these can be piles, or other means of providing the required material. In addition, when we refer to BTU/lb, it is the heat content of the material on a weight basis, so can be expressed in many different methods. As detailed in FIG. 11, the analyzer can be used to blend material to a specific composition that, in the case where one of the materials is waste or AF, can be used as a prepared blend that is suitable for use as a fuel.

The information from the analyzer does not have to provide all of the required information for analysis. For example, the belt loading is typically provided by a separate sensor. The moisture reading may be provided by an external moisture meter. Alternately, external sensors can be added that can be used to improve the analysis results. For example, dual energy gamma detectors can be used to provide an absolute measurement of the organic and inorganic material in the AF. This in turn can be used to adjust the measurement information from the analyzer. In some cases, there will be readings that are not suitably accurate from the analyzer. In this case, it may be necessary to use separate measurement equipment to provide the required data and information. The analyzer does not have to provide all of the required measurement information, but the information it provides is used to ensure that the material is acceptable as a fuel.

These blending approaches detailed above are not new. Raw material blending has been done with PGNAA systems for over 20 years, and is in widespread use throughout the cement industry. Extensive equipment, processes, and blending software is widely available that helps in the blending process. Any of the blending approaches that are now used for raw material blending, whether it is in discrete piles, done in silos, done in layers, or done in real-time using multiple 'sweetners', can be used to blend the alternative fuels to specific target blends. In addition, there are sites that blend AF. These sites use labs to do sample analysis of the AF to ensure no contaminants and to have an approximate composition of the AF, and then the AF is mixed together.

There are many different ways of using the measurement data to calculate material heat value (expressed as BTU/lb in this patent). It is possible to use the system measurement data and associated peripheral data to estimate the AF BTU/lb, and allow blending to specific BTU targets, or to verify that the material is acceptable for use as a fuel. Another benefit of this new design of analyzer is that it is possible to measure trace contaminants, and greatly improve the performance of these analyzers. Thus this has other applications such as measuring and controlling Mercury content of raw materials, measuring trace contaminants in bulk material, controlling the amount of trace contaminants in bulk material, blending using the measurement information, sorting using the measurement information, faster more accurate sorting of coal with different ash contents, and other applications that benefit from the improved system performance.

Figure 12:
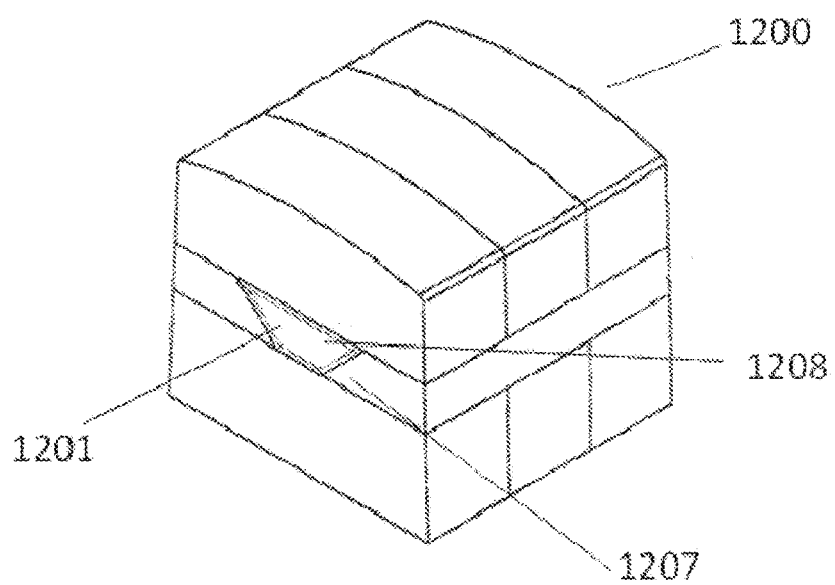
FIG. 12 is a perspective view of a high performance PGNAA analyzer.

FIG. 12 is a perspective view of an embodiment of a high performance PGNAA analyzer 1200. As illustrated in FIG. 12, a conveying mechanism 1208 may extend through the analyzer 1200. The conveying mechanism 1208 may include a conveyor 1201 with sides 1207. Sides 1207 may be angled relative to conveyor 1201 as disclosed herein.

Those of skill will appreciate that the various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the invention. In addition, the grouping of functions within a module, block, or step is for ease of description. Specific functions or steps can be moved from one module or block without departing from the invention.

The various illustrative logical blocks and modules described in connection with the embodiments disclosed herein can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor (e.g., of a computer), or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

The above description of the disclosed embodiments is provided to enable any person skilled in the art to make or use the invention. Various modifications to the embodiments of the analyzer will be readily apparent to those skilled in the art, and the generic principles described herein can be applied to other embodiments without departing from the spirit or scope of the invention. Thus, it is to be understood that the description and drawings presented herein represent a presently preferred embodiment of the analyzer and are therefore representative of the subject matter which is broadly contemplated by the present invention. It is further understood that the scope of the present invention fully encompasses other embodiments that may become obvious to those skilled in the art.

We claim:

1. An analyzer for measuring an elemental composition of materials, the analyzer comprising:
    a conveying mechanism including a conveyor extending in a horizontal direction,
    a first side wall extending adjacent the conveyor, and
    a second side wall extending adjacent the conveyor opposite the first side wall forming a detection zone;
    at least one neutron source located proximate the detection zone;
    at least one detector located proximate the detection zone and on a side of the detection zone adjacent the neutron source;
    a top extending from the first side to the second side forming a main transport chamber, the main transport chamber surrounding the detection zone; and
    wherein the conveyor includes a porous material extending between the first side and the second side, and an air chamber located next to the detection zone, the air chamber being separated from the transport chamber by the porous material.

2. The analyzer of claim 1, further comprising a first array of detectors proximate the first side wall including the at least one detector, and a second array of detectors proximate the second side wall; wherein the first array of detectors and the second array of detectors are configured to detect trace amounts of elements including contaminants.

3. The analyzer of claim 2, further comprising an array of neutron sources including the at least one neutron source located proximate the conveyor.

4. The analyzer of claim 1, wherein the first side wall and the second side wall are angled substantially perpendicular to the conveyor forming a rectangular detection zone.

5. The analyzer of claim 1, wherein the first side wall and the second side wall are angled from 50 degrees to 130 degrees relative to the conveyor.

6. The analyzer of claim 1, wherein the at least one neutron source is configured to emit fast neutrons, thermal neutrons, or a combination of both.

7. The analyzer of claim 1, further comprising a processing module configured to determine a calorific value of alternative fuel materials based at least on the elemental composition measured by the at least one detector.

8. A process of analyzing bulk materials using an on-line nuclear based analyzer including at least one neutron source and at least one detector, the process comprising:
    conveying the bulk materials to the on-line analyzer;
    conveying the bulk materials through the on-line analyzer on a conveying mechanism including a conveyor extending in a horizontal direction, a first side wall adjacent the conveyor and a second side wall adjacent the conveyor forming a detection zone;
    directing neutrons at the bulk materials using the at least one neutron source located proximate the detection zone;

quantitatively and non-destructively measuring an elemental composition of the bulk materials using the at least one detector located proximate the detection zone and located on an adjacent side of the detection zone;

wherein conveying the bulk materials through the on-line analyzer further includes conveying the bulk material over the conveyor fluidized by air; and wherein the conveyor includes a porous material and an air chamber separated from the detection zone by the porous material; and wherein the bulk material is a powder and the air is supplied from the air chamber through the porous material.

9. The process of claim 8, wherein the process includes detecting trace amounts of amounts of materials within the bulk materials using the array of detectors.

10. The process of claim 9, wherein quantitatively and non-destructively measuring an elemental composition of the bulk materials and detecting trace amounts of amounts of materials within the bulk materials also uses a second array of detectors located proximate the second side wall.

11. The process of claim 9, wherein directing neutrons at the bulk materials also uses an array of neutron sources located proximate the conveyor.

12. The process of claim 9, further comprising:
directing the bulk materials to a first location when trace materials of contaminants above a predetermined level is detected; and
directing the bulk material to a second location when trace materials of contaminants below the predetermined level is detected.

13. The process of claim 12, further comprising blending the bulk material from the first location with the bulk material from the second location to include an amount of contaminants below a second predetermined level.

14. The process of claim 8, wherein the bulk material is transported by gravity by having the conveyor on a slight angle to horizontal.

* * * * *